(12) United States Patent
Aginsky et al.

(10) Patent No.: US 10,709,374 B2
(45) Date of Patent: Jul. 14, 2020

(54) SYSTEMS AND METHODS FOR ASSESSMENT OF A MUSCULOSKELETAL PROFILE OF A TARGET INDIVIDUAL

(71) Applicant: Physimax Technologies Ltd., Kibbutz Glil-Yam (IL)

(72) Inventors: Kerith Dana Aginsky, Tel-Aviv (IL); David Kahani, Yavne (IL); Ram Daniel Shalev, Herzliya (IL); Maya Cal'E-Benzoor, Haifa (IL); Arie Gofer, Even Yehuda (IL)

(73) Assignee: Physimax Technologies Ltd., Kibbutz Glil-Yam (IL)

( * ) Notice: Subject to any disclaimer, the term of this patent is extended or adjusted under 35 U.S.C. 154(b) by 162 days.

(21) Appl. No.: 15/918,131

(22) Filed: Mar. 12, 2018

(65) Prior Publication Data

US 2019/0274614 A1    Sep. 12, 2019

(51) Int. Cl.
| | | |
|---|---|---|
| *G06K 9/00* | (2006.01) | |
| *A61B 5/22* | (2006.01) | |
| *A61B 5/11* | (2006.01) | |
| *A61B 5/00* | (2006.01) | |
| *G06T 7/20* | (2017.01) | |

(52) U.S. Cl.
CPC ............ *A61B 5/224* (2013.01); *A61B 5/0013* (2013.01); *A61B 5/0075* (2013.01);
(Continued)

(58) Field of Classification Search
CPC ..... A61B 5/224; A61B 5/1107; A61B 5/1128; A61B 5/1121; A61B 5/4884;
(Continued)

(56) References Cited

U.S. PATENT DOCUMENTS

| | | |
|---|---|---|
| 8,527,217 B2 | 9/2013 | Moodie |
| 2007/0203430 A1* | 8/2007 | Lang ...................... A61B 5/055 600/587 |

(Continued)

FOREIGN PATENT DOCUMENTS

WO    WO 2019/175860    9/2019

OTHER PUBLICATIONS

Cattagni et al (Ankle muscle strength discriminates fallers from non-fallers, Faculte des sciences du sports-UFRSTAPS, Universite de Bourgogne, Dijon, France, Dec. 19, 2014) (Year: 2014).*

(Continued)

*Primary Examiner* — Amara Abdi

(57) ABSTRACT

There is provided a method of indirectly estimating muscle strength ratio, comprising: receiving images and associated body part locations of a target individual, wherein the images depict the target individual performing a first and a second defined movement, identifying first image(s) depicting the first defined movement, and obtaining an associated first set of body part locations, identifying second image(s) depicting the second defined movement, and obtaining an associated second set of body part locations, computing a first image-metric according to the first set of body part locations, computing a second image-metric according to the second set of body part locations, computing an image-parameter according to the first and second image-metrics, and converting the image-parameter to an estimate of a measured-parameter indicative of strength measurement ratio of the target muscle(s) obtained by a dynamometer, according to correlation between image-parameters and measured-parameters obtained based on the dynamometer performing empirical measurements.

35 Claims, 3 Drawing Sheets

(52) U.S. Cl.
CPC .......... *A61B 5/0077* (2013.01); *A61B 5/1107* (2013.01); *A61B 5/1121* (2013.01); *A61B 5/1128* (2013.01); *A61B 5/4571* (2013.01); *A61B 5/4585* (2013.01); *A61B 5/4884* (2013.01); *A61B 5/7246* (2013.01); *A61B 5/746* (2013.01); *A61B 2576/00* (2013.01); *G06T 7/20* (2013.01); *G06T 2207/10016* (2013.01); *G06T 2207/30196* (2013.01)

(58) Field of Classification Search
CPC ... A61B 5/4571; A61B 5/4585; A61B 5/7246; A61B 5/746; A61B 5/0075; A61B 5/0013; A61B 5/0077; A61B 2576/00; G06T 2207/30196; G06T 2207/10016; G06T 7/20
See application file for complete search history.

(56) References Cited

U.S. PATENT DOCUMENTS

| | | |
|---|---|---|
| 2010/0049095 A1 | 2/2010 | Bunn et al. |
| 2011/0196262 A1 | 8/2011 | McLeod et al. |
| 2014/0140596 A1* | 5/2014 | Kawaguchi ........ G06K 9/00348 382/128 |
| 2014/0174174 A1 | 6/2014 | Uehara et al. |
| 2015/0117728 A1 | 4/2015 | Choi et al. |
| 2015/0297128 A1 | 10/2015 | Shield et al. |
| 2015/0318015 A1 | 11/2015 | Bose et al. |
| 2017/0172465 A1* | 6/2017 | Osorio ................. A61B 5/0205 |

OTHER PUBLICATIONS

Patterson, (The relationship between the Hamstrings to Quadriceps strength ratio and anterior cruciate ligament forces, Thesis from east Carolina university, May 2016) (Year: 2016).*

Beumer et al (Grip strength ratio: a grip strength measurement that correlates well with DASH score in different hand/wrist conditions, Beumer and Lindau BMC Musculoskeletal Disorders, pp. 1-6, 2014) (Year: 2014).*

Strasser et al, (Association between ultrasound measurements of muscle thickness, pennation angle, echogenicity and skeletal muscle strength in the elderly, AGE (2013) 35:2377-2388) (Year: 2013).*

Lee et al (The reliability and validity of a video-based method for assessing hamstring strength in football players, Journal of Exercise Science and Fitness, 2017, pp. 18-21) (Year: 2017).*

Williams et al, ("Electromyographic Analysis of Hip Knee Exercise: a continuum from early rehabilitation to enhancing performance", university of Hertfordshire, Oct. 2013, pp. 10-141) (Year: 2013).*

International Search Report and the Written Opinion Dated Jun. 26, 2019 From the International Searching Authority Re. Application No. PCT/IL2019/050241. (19 Pages).

Cattagni et al. "Ankle Muscle Strength Discriminates Fallers From Non-Fallers", Frontiers in Aging Neuroscience, 6(Art.336): 1-7, Published online Dec. 19, 2014.

Lee et al. "The Reliability and Validity of a Video-Based Method for Assessing Hamstring Strength in Football Players", Journal of Exercise Science & Fitness, 15(1): 18-21, Available Online Apr. 28, 2017.

Patterson "The Relationship Between the Hamstring to Quadriceps Strength Ratio and Anterior Cruciate Ligament Forces", A Thesis in Partial Fulfillment of the Requirements for the Degree of Masters of Science in Kinesiology, Biomechanics Concentration Presented to the Faculty of the Department of Kinesiology, East Carolina University, USA, p. 1-96, May 2016.

Williams "Electromyographic Analysis of Hip and Knee Exercises: A Continuum From Early Rehabilitation to Enhancing Performance", Submitted in Partial Fulfillment of the Requirements of the Degree of MPhil, University of Hertfordshire, UK, p. 1-141, Oct. 2013.

* cited by examiner

SYSTEMS AND METHODS FOR ASSESSMENT OF A MUSCULOSKELETAL PROFILE OF A TARGET INDIVIDUAL

BACKGROUND

The present invention, in some embodiments thereof, relates to physical evaluation and, more specifically, but not exclusively, to systems and methods for assessment of a musculoskeletal profile of a target individual.

Individuals undergo physical assessment for a variety of reasons, for example, to determine whether muscle strength is sufficient for performing certain athletic activities, to estimate risk of injury due to inadequate muscle strength, to assess extent of an injury, to assess improvement in performance, functional and/or game technique. The individuals may be athletes seeking to improve athletic performance, healthy individuals that have been injured, and/or patients with medical conditions that are in a rehabilitation program (e.g., due to stroke, brain injury, orthopedic injury, and Parkinson's disease). Assessment is routinely performed by a dynamometer that physically measures muscle strength of the target individual, for example, the individual physically pulling or pushing on a level which may be set at varying degrees of resistance.

SUMMARY

According to a first aspect, a system for indirectly estimating a value indicative of muscle strength ratio of at least one target muscle of a target individual based on an analysis of a plurality of digital images, comprises: a non-transitory memory having stored thereon a code for execution by at least one hardware processor of a computing device, the code comprises: code for receiving, from at least one sensor, a video including a plurality of images and associated plurality of body part locations of a target individual corresponding to the plurality of images, wherein the video depicts the target individual performing a physical movement test comprising a first defined movement and a second defined movement, code for identifying at least one first image of the plurality of imaged depicting the target individual performing the first defined movement, and obtaining a first set of body part locations associated with the at least one first image, code for identifying at least one second image of the plurality of imaged depicting the target individual performing the second defined movement, and obtaining a second set of body part locations associated with the at least one second image, code for computing a first image-metric according to the first set of body part locations associated with the at least one first image, and computing a second image-metric according to the second set of body part locations associated with the at least one second image, code for computing an image-parameter according to the first image-metric and the second image-metric, and code for converting the image-parameter to an estimate of a measured-parameter indicative of strength measurement ratios of the at least one target muscle obtained by a dynamometer, according to correlation code that correlates between image-parameters and measured-parameters obtained based on the dynamometer performing empirical measurements of application of an exerted force of the at least one target muscle by each of a plurality of other subjects.

According to a second aspect, a method of indirectly estimating a value indicative of muscle strength ratio of at least one target muscle of a target individual based on an analysis of a plurality of digital images, comprises: receiving, from at least one sensor, a video including a plurality of images and associated plurality of body part locations of a target individual corresponding to the plurality of images, wherein the video depicts the target individual performing a physical movement test comprising a first defined movement and a second defined movement, identifying at least one first image of the plurality of imaged depicting the target individual performing the first defined movement, and obtaining a first set of body part locations associated with the at least one first image, identifying at least one second image of the plurality of imaged depicting the target individual performing the second defined movement, and obtaining a second set of body part locations associated with the at least one second image, computing a first image-metric according to the first set of body part locations associated with the at least one first image, and computing a second image-metric according to the second set of body part locations associated with the at least one second image, computing an image-parameter according to the first image-metric and the second image-metric, and converting the image-parameter to an estimate of a measured-parameter indicative of strength measurement ratios of the at least one target muscle obtained by a dynamometer, according to correlation between image-parameters and measured-parameters obtained based on the dynamometer performing empirical measurements of application of an exerted force of the at least one target muscle by each of a plurality of other subjects.

According to a third aspect, a computer program product for indirectly estimating a value indicative of muscle strength ratio of at least one target muscle of a target individual based on an analysis of a plurality of digital images, comprises: a non-transitory memory having stored thereon a code for execution by at least one hardware processor of a computing device, the code comprises: instructions for receiving, from at least one sensor, a video including a plurality of images and associated plurality of body part locations of a target individual corresponding to the plurality of images, wherein the video depicts the target individual performing a physical movement test comprising a first defined movement and a second defined movement, instructions for identifying at least one first image of the plurality of imaged depicting the target individual performing the first defined movement, and obtaining a first set of body part locations associated with the at least one first image, instructions for identifying at least one second image of the plurality of imaged depicting the target individual performing the second defined movement, and obtaining a second set of body part locations associated with the at least one second image, instructions for computing a first image-metric according to the first set of body part locations associated with the at least one first image, and computing a second image-metric according to the second set of body part locations associated with the at least one second image, instructions for computing an image-parameter according to the first image-metric and the second image-metric, and instructions for converting the image-parameter to an estimate of a measured-parameter indicative of strength measurement ratios of the at least one target muscle obtained by a dynamometer, according to correlation code that correlates between image-parameters and measured-parameters obtained based on the dynamometer performing empirical measurements of application of an exerted force of the at least one target muscle by each of a plurality of other subjects.

At least some of the systems, methods, apparatus, and/or code instructions described herein relate to the technical problem of indirectly estimating values indicative of muscle strength ratio for a target individual without actually directly performing measurements of the target individual by a dynamometer.

At least some of the systems, methods, apparatus, and/or code instructions described herein improve performance of a computing device, by enabling the computing device to perform functions that have not before been performed by a computing device. The systems, methods, apparatus, and/or code instructions described herein enable the computing device to estimate values for a target individual based on images, where the values are indirect estimates of measurements performed by a dynamometer, without actually performing measurements by the dynamometer. Effectively, the dynamometer is replaced by a sensor(s) that at least captures images of the target individual, and code instructions executed by processor(s) of the computing device.

At least some of the systems, methods, apparatus, and/or code instructions described herein operate differently than standard manual procedures for computing force-based values for the target individual. Such manual procedures are based on manually measuring one or more forces physically generated by the target individual, by manually setting and using a dynamometer. In contrast, the systems, methods, apparatus, and/or code instructions described herein are automated, based on an automated analysis of images captured of the target individual, without actually performing any manual measurements using dynamometers on the target individual.

In a further implementation form of the first, second, and third aspects, the first defined movement is based on no significant resistance of a target muscle, and wherein the second defined movement is based on at least partial resistance of the target muscle.

In a further implementation form of the first, second, and third aspects, the first defined movement is based on a first partial resistance of a target muscle, and wherein the second defined movement is based on a second resistance of the target muscle greater than the first partial resistance.

In a further implementation form of the first, second, and third aspects, the first defined movement and the second defined movement are indicative of force proportion of muscle groups.

In a further implementation form of the first, second, and third aspects, the first defined movement and the second defined movement indicative of force proportion of muscle groups are selected from the group consisting of: flexion, extension, abduction, adduction, internal rotation, external rotation.

In a further implementation form of the first, second, and third aspects, the first image-metric and the second-image metric are selected from the group comprising: joint angle, rotation amount, abduction amount, adduction amount, flexion amount, and extension amount.

In a further implementation form of the first, second, and third aspects, the first defined movement comprises an unsupported single leg squat (USLS) and the second defined movement comprises a supported single leg squat (SSLS).

In a further implementation form of the first, second, and third aspects, the first image-metric comprises an unsupported knee valgus, the second image-metric comprises a supported knee valgus, and the image-parameter is computed as: (supported knee valgus−unsupported knee valgus)/supported knee valgus×100, wherein the image-parameter is correlated to the measured-parameter indicative of a hip adductor/abductor strength ratio.

In a further implementation form of the first, second, and third aspects, the first image-metric comprises an unsupported hip flexion, the second image-metric comprises a supported hip flexion, and the image-parameter is computed as: (supported hip flexion−unsupported hip flexion)/supported hip flexion×100, wherein the image-parameter is correlated to the measured-parameter indicative of a hip extensor/flexor muscle strength ratio.

In a further implementation form of the first, second, and third aspects, the first image-metric comprises an unsupported anterior knee displacement, the second image-metric comprises a supported anterior knee displacement, and the image-parameter is computed as: (supported anterior knee displacement−unsupported anterior knee displacement)/supported anterior knee displacement×100, wherein the image-parameter is correlated to the measured-parameter indicative of an eccentric hamstring/eccentric quadriceps muscle strength ratio.

In a further implementation form of the first, second, and third aspects, the first image-metric comprises a first maximal knee flexion (KF) during USLS, and the second image-metric comprises a second maximal KF during SSLS, wherein the image-parameter comprises a dynamic knee ratio (DKR) denoting the percentage difference between the second maximal KF and the first maximal KF, and wherein the DKR is converted to a value indicative of hamstring muscle strength.

In a further implementation form of the first, second, and third aspects, the correlation code includes code for correlating between DKR and a concentric Hamstring/Quadriceps strength (H/Q) ratio.

In a further implementation form of the first, second, and third aspects, the correlation code includes code for a negative linear function for correlating between decreasing DKR values and increasing H/Q ratio values.

In a further implementation form of the first, second, and third aspects, the correlation code includes code for correlating between DKR and a concentric hamstring peak torque.

In a further implementation form of the first, second, and third aspects, the correlation code includes code for correlating between DKR and a concentric hamstring PT/BW (peak torque/body weight).

In a further implementation form of the first, second, and third aspects, the system further comprises code instructions for and/or the method further comprises and/or the computer program product further comprises additional instructions for generating an alert indicative of weakness in the hamstring muscle relative to the quadriceps muscle when the DKR is greater than a threshold.

In a further implementation form of the first, second, and third aspects, the system further comprises code instructions for and/or the method further comprises and/or the computer program product further comprises additional instructions for computing the DKR according to the relationship: DKR=(maximal KF during SLSS−maximal KF during USLS)/maximal KF during SLSS×100.

In a further implementation form of the first, second, and third aspects, the system further comprises code instructions for and/or the method further comprises and/or the computer program product further comprises additional instructions for generating an alert indicative of weakness in a first target muscle relative to a second target muscle when the image-parameter is greater than a threshold selected according to a population that is matched to a profile of the target individual.

In a further implementation form of the first, second, and third aspects, the threshold is about 15-20%.

In a further implementation form of the first, second, and third aspects, the threshold is selected according to the bottom twentieth percentile values of the population.

In a further implementation form of the first, second, and third aspects, the converting is performed without the target individual undergoing measurements by the dynamometer.

In a further implementation form of the first, second, and third aspects, the dynamometer comprises an isokinetic strength testing device.

In a further implementation form of the first, second, and third aspects, the system further comprises code instructions for and/or the method further comprises and/or the computer program product further comprises additional instructions for computing the first and second set of body part locations from at least one of frontal and sagittal plane two dimensional (2D) images.

In a further implementation form of the first, second, and third aspects, the first and second set of body part locations include 3D body joint locations.

In a further implementation form of the first, second, and third aspects, the correlation code includes a statistical classifier that classifies the image-parameter into a classification category indicative of strength of a target muscle.

In a further implementation form of the first, second, and third aspects, the selecting of the at least one first image and the at least one second image from the video comprises: computing at least one frame-value for each of the plurality of images, each frame-value computed according to the body part locations of the target individual, analyzing the at least one frame value computed for each of the plurality of images to identify a plurality of image state-frames, each image state-frame corresponding to a certain state of a plurality of states of the certain physical movement test, and identifying the first and second defined movements according to corresponding image state-frames based on a predefined order of the corresponding plurality of states of the physical movement test.

In a further implementation form of the first, second, and third aspects, the analyzing is performed according to a set-of-rules applied to the at least one frame-value.

In a further implementation form of the first, second, and third aspects, the certain state of the plurality of states is selected from the group consisting of Starting Position, and Maximum Displacement.

In a further implementation form of the first, second, and third aspects, the at least one frame value is selected from the group consisting of: position of at least one joint, angle of at least one joint, and angle between at least two body parts.

In a further implementation form of the first, second, and third aspects, the first defined movement and the second defined movement are based on one or more members of the group consisting of: LESS, Shoulder Rotation, CMJ, Repetitive-CMJ, Single Leg Squat test, Full squat, single leg hop, SL-drift, and Dorsiflexion test, Hip Rotation test.

In a further implementation form of the first, second, and third aspects, the at least one sensor comprises at least one video camera that captures the video and code for analyzing the video for computing the body location data.

In a further implementation form of the first, second, and third aspects, the at least one sensor comprises a 3D kinetic sensor that captures the video and captures depth data, wherein the depth data is mapped to the video, wherein the body part locations are computed according to the depth data.

In a further implementation form of the first, second, and third aspects, the plurality of images are selected from the group consisting of: visual images captured by at least one visual sensor, depth images captured by at least one depth sensor, and infrared images captured by at least one infrared sensors.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DETAILED DESCRIPTION

Figure 1:
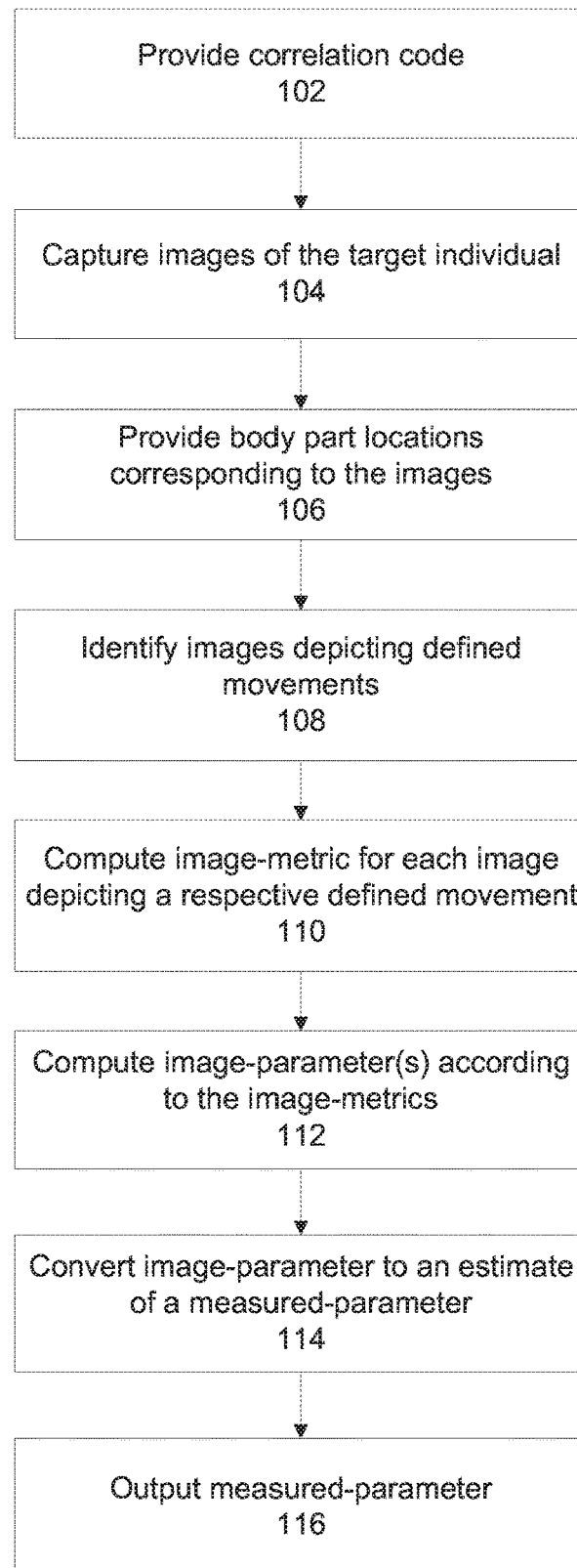
FIG. 1 is a flowchart of a method of indirectly estimating a value indicative of ratio between muscle strength of target muscle(s) of a target individual based on an analysis of digital image(s)

The present invention, in some embodiments thereof, relates to physical evaluation and, more specifically, but not exclusively, to systems and methods for assessment of a musculoskeletal profile of a target individual.

As used herein, the term dynamometer refers to a device designed to physically measure a force applied by a target individual. The dynamometer is meant to include a variety of non-imaging methods and/or devices that measure forces applied by the target individual. Exemplary dynamometers include, but are not necessarily limited to: handheld dynamometer, isokinetic dynamometer, force plate, force mat, or other systems and/or methods based on derivation of the force from other force applications measurements (e.g., calculating the force exerted by the athlete muscles when weight lifting based on the weight the athlete is lifting and the body mass of the athlete).

An aspect of some embodiments of the present invention relates to systems, an apparatus, methods, and/or code instructions (e.g., stored in a data storage device, executable by one or more hardware processors) for indirectly estimating a value indicative of ratio between muscle strength of target muscles of a target individual (also referred to herein as muscle strength ratio) based on an analysis of images (e.g., video) and/or body part locations of the target individual corresponding to the images, captured by one or more sensors (e.g., camera, video camera, kinetic sensor), optionally an image sensor (e.g., camera, video camera) without a dynamometer performing the muscle strength measurements. The values indicative of ratio between muscle strength of target muscles computed from the analysis of the images and/or body part locations are correlated to measurements previously performed by the dynamometer on other subjects.

The images (e.g., extracted from a video or taken as a snapshot) are captured while the target individual is performing a certain physical movement task that includes two or more defined movements. Body part locations corresponding to the images include, for example, a set of three dimensional (3D) coordinates of joints and/or other body parts of the target individual appearing in the images such as limbs, head, neck, torso and abdomen, and/or anatomical landmarks such as eyes, ears, nose, and spine, and/or body contours, and/or bone outline indicative of location of underlying bones. The body part locations corresponding to the images may be outputted by a 3D sensor that captures depth location data and optionally an associated visual image. Alternatively or additionally, the body part locations are computed from the images themselves, for example, by code that identifies the body parts within the images and comprise the location of each body part within a 2D and/or 3D coordinate system.

For simplicity of explanation, two sets of body part locations are described as being computed and processed to compute respective image-metrics. However, it is to be understood that three or more sets of body part locations may be computed and processed to compute respective image-metrics. It is noted that in some cases a single set of body parts may be computed and processed to compute two or more image-metrics from the same single set.

One or more images that depict the target individual performing a first defined movement are identified. A first set of body part location is associated with the identified images. A first image-metric is computed according to the first set of body part locations. One or more other images that depict the target individual performing a second defined movement are identified. A second set of body part locations is associated with the one or more other images. A second image-metric is computed according to the second set of body part locations. An image-parameter is computed according to the first and second image-metrics. The image-parameter is converted into an estimate of a measure-parameter indicative of indirect muscle strength of target muscle(s) of the target individual. The measure-parameter, which is an indirect measure of muscle strength ratio is in contrast to direct measures of muscle strength that are obtained by a dynamometer. The image-parameter is converted into the estimate of the measure-parameter by correlation code that correlates between image-parameters and measured-parameters based on empirical measurements of the dynamometer of application of an exerted muscle force by multiple other subjects.

At least some of the systems, methods, apparatus, and/or code instructions described herein relate to the technical problem of indirectly estimating values indicative of muscle strength ratio for a target individual without actually directly performing measurements of the target individual by a dynamometer.

At least some of the systems, methods, apparatus, and/or code instructions described herein improve performance of a computing device, by enabling the computing device to perform functions that have not before been performed by a computing device. The systems, methods, apparatus, and/or code instructions described herein enable the computing device to estimate values for a target individual based on images, where the values are indirect estimates of measurements performed by a dynamometer, without actually performing measurements by the dynamometer. Effectively, the dynamometer is replaced by a sensor(s) that at least captures images of the target individual, and code instructions executed by processor(s) of the computing device.

At least some of the systems, methods, apparatus, and/or code instructions described herein operate differently than standard manual procedures for computing force-based values for the target individual. Such manual procedures are based on manually measuring one or more forces physically generated by the target individual, by manually setting and using a dynamometer. In contrast, the systems, methods, apparatus, and/or code instructions described herein are automated, based on an automated analysis of images captured of the target individual, without actually performing any manual measurements using dynamometers on the target individual.

When the features related to by the systems, methods, apparatus, and/or code instructions described herein are taken as a whole, the combination of the features amounts to significantly more than a simple mathematical calculation of values that correspond to measurements performed by a dynamometer. The systems, methods, apparatus, and/or code instructions described herein do not merely relate to mathematical computations (e.g., correlation), but relate to the particular data collected, stored, and the way the data is captured by images and analyzed.

At least some of the systems, methods, apparatus, and/or code instructions described herein improve an underling technical process within the technical field of image processing, in particular within the field of assessment of a musculoskeletal profile.

At least some of the systems, methods, apparatus, and/or code instructions described herein generate new data in the form of the correlation code that correlates between values computed from images and values based on measurements performed by a dynamometer.

Accordingly, at least some of the systems, methods, apparatus, and/or code instructions described herein are tied to physical real-life components, for example, sensor(s) that capture the images and/or body part locations that are analyzed, physical data storage devices and/or memory, physical displays and/or physical hardware processors, to overcome an actual technical problem arising in performing an automated assessment of a musculoskeletal profile.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

As used herein, the term image may refer to a video which includes multiple images, for example, the image(s) is identified as one or more frames of the video. The term image may sometimes refer to still images, which may be captured independently, for example, by a high speed camera that captures images at a frame rate that is higher or lower than the frame rate captured by a video camera.

As used herein, the term dynamometer refers to a device for measuring muscle strength of a target individual based on physical contact between a component of the measuring device and the target individual, for example, an ankle attachment that contacts the ankle of the target individual, and a handle that contacts the hand of the target individual. The dynamometer may include, for example, an isokinetic strength testing device.

Figure 2:
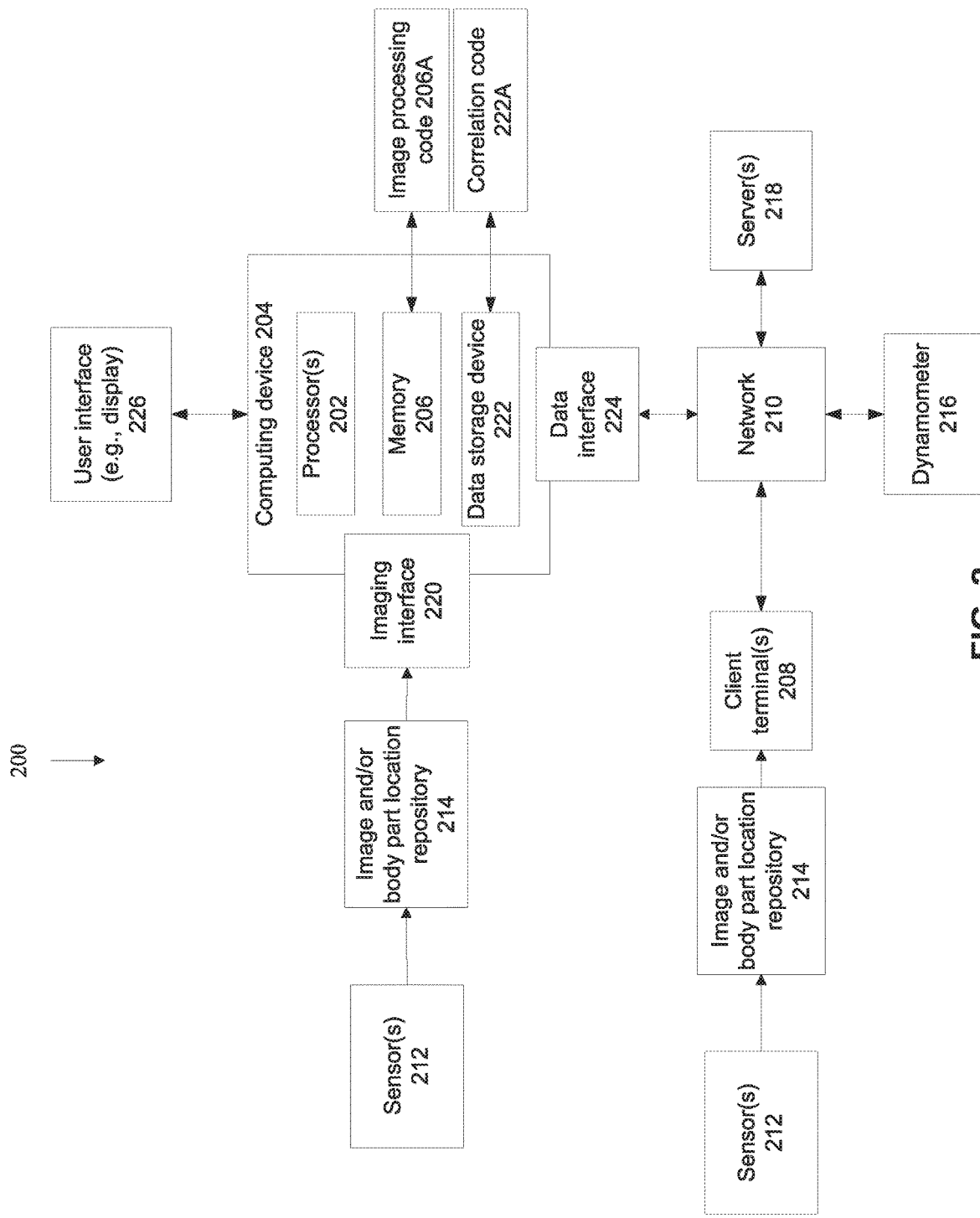
FIG. 2 is a block diagram of components of a system for indirectly estimating a value indicative of ratio between muscle strength of target muscle(s) of a target individual based on an analysis of digital image(s) and/or for creating and/or updating correlation code that correlates between image-parameters computed based on images and measured-parameters obtained by empirical measurements of a dynamometer, in accordance with some embodiments of the present invention.

Reference is now made to FIG. 1, which is a flowchart of a method of indirectly estimating a value indicative of ratio between muscle strength of target muscle(s) of a target individual based on an analysis of digital image(s), in accordance with some embodiments of the present invention. Reference is also made to FIG. 2, which is a block diagram of components of a system 200 for indirectly estimating a value indicative of ratio between muscle strength of target muscle(s) of a target individual based on an analysis of digital image(s) and/or for creating and/or updating correlation code that correlates between image-parameters computed based on images and measured-parameters obtained by empirical measurements of a dynamometer, in accordance with some embodiments of the present invention. System 200 may implement the acts of the method described with reference to FIG. 1, optionally by a hardware processor(s) 202 of a computing device 204 executing code instructions 206A stored in a data storage device 206.

Computing device 204 may be implemented as, for example, a client terminal, a server, a virtual machine, a computing cloud, a mobile device, a desktop computer, a thin client, a Smartphone, a Tablet computer, a laptop computer, a wearable computer, glasses computer, and a watch computer.

Multiple architectures of system 200 based on computing device 204 may be implemented. For example:

Computing device 204 may be implemented as a standalone device (e.g., kiosk, client terminal, smartphone) that include locally stored code instructions 206A that implement one or more of the acts described with reference to FIG. 1. The locally stored instructions may be obtained from another server, for example, by downloading the code over the network, and/or loading the code from a portable storage device.

Computing device 204 executing stored code instructions 206A, may be implemented as one or more servers (e.g., network server, web server, a computing cloud, a virtual server) that provides services (e.g., one or more of the acts described with reference to FIG. 1) to one or more client terminals 208 over a network 210. For example, providing software as a service (SaaS) to the client terminal(s) 208, providing software services accessible using a software interface (e.g., application programming interface (API), software development kit (SDK)), providing an application for local download to the client terminal(s) 208, providing an add-on to a web browser running on client terminal(s) 208, and/or providing functions using a remote access session to the client terminals 208, such as through a web browser executed by client terminal 208 accessing a web sited hosted by computing device 204.

As used herein, the term camera may sometimes be interchanged with the term sensor and/or with the term image sensor.

Computing device 204 receives images (e.g., video) and/or body part locations of the target individual captured by one or more sensors(s) 212. The body part locations correspond to the captured images. The body part locations may be computed based on an analysis of the captured images (e.g., based on visual markers denoting the body part locations, and/or by code that performs a 3D analysis of the images), and/or the body part locations may be computed by a kinetic sensor component of sensor(s) 212 that captures depth data.

The images may be, for example, visual images captured by a visual sensor(s) and/or image sensor(s), depth images captured by a depth sensor(s), and/or infrared images captured by an infrared sensor(s).

The images may be two dimensional (2D), and/or three dimensional (3D). Images may be captured by one or more sensors 212, for example, two or three camera positioned at various angles relative to the target individual. The images (e.g., 2D images) captured from the multiple cameras may be analyzes to compute a set of 3D images. Sensor(s) 212 may include a video camera that capture video (i.e., a sequence of images) and/or that capture still images. Sensor(s) 212 may be implemented as a 3D sensor that includes sensing of depth and/or a 3D kinetic sensor(s).

In one implementation, sensor(s) 212 includes video camera(s) that captures the video and code for analyzing the video for computing the body location data. In another implementation, sensor(s) 212 includes a 3D sensor and/or depth sensor that captures the video and captures depth data, where the depth data is mapped to the video, and the body part locations are computed according to the depth data. Exemplary sensor(s) 212 may be based on, for example, infra-red, dual cameras, radiofrequency (RF) waves, and laser projection.

Sensor(s) 212 may be implemented as an external device and/or integrated into a computing device, for example, an IP camera and/or camera of a smartphone.

Images and/or body part locations captured by sensor(s) 212 may be stored in an image and/or body part location data repository 214, for example, a storage server, a computing cloud, virtual memory, and a hard disk. The images and/or body part location stored in image and/or body part location repository 214 may include images and/or body part location of sample individuals for computation and/or updating of correlation code (e.g., 222A) as described herein, and/or may include images and/or body part location of the target individual for which the image-metrics and/or image-parameters are computed.

Computing device 204 may receive the images and/or body part locations from sensor(s) 212 and/or image and/or body part location repository 214 via one or more imaging interfaces 220, for example, a wire connection (e.g., physical port), a wireless connection (e.g., antenna), a local bus, a port for connection of a data storage device, a network interface card, other physical interface implementations, and/or virtual interfaces (e.g., software interface, virtual private network (VPN) connection, application programming interface (API), software development kit (SDK)).

Alternatively or additionally, computing device 204 receives the images and/or body part locations from sensor(s) 212 and/or image and/or body part location repository 214 via client terminal(s), over network 210. For example, the image are captured by an independent digital camera and/or digital camera built into the client terminal (e.g., still and/or video), stored by client terminal 208, and uploaded by client terminal 208 over network 210 to a website hosted by computing device 204. Computing device 204 may analyze the image to compute the body part locations corresponding to the images.

Hardware processor(s) 202 may be implemented, for example, as a central processing unit(s) (CPU), a graphics processing unit(s) (GPU), field programmable gate array(s) (FPGA), digital signal processor(s) (DSP), and application specific integrated circuit(s) (ASIC). Processor(s) 202 may include one or more processors (homogenous or heterogeneous), which may be arranged for parallel processing, as clusters and/or as one or more multi core processing units.

Memory 206 (also referred to herein as a program store, and/or data storage device) stores code instruction for execution by hardware processor(s) 202, for example, a random access memory (RAM), read-only memory (ROM), and/or a storage device, for example, non-volatile memory, magnetic media, semiconductor memory devices, hard drive, removable storage, and optical media (e.g., DVD, CD-ROM). For example, program store 206 may store image processing code 206A that implements one or more acts and/or features of the method described with reference to FIG. 1.

Computing device 204 may include a data storage device 222 for storing data, for example, correlation code 222A that stores codes instructions that when executed by processor(s) 202 correlate between values computed from images and values measured by a dynamometer. Data storage device 222 may be implemented as, for example, a memory, a local hard-drive, a removable storage device, an optical disk, a storage device, and/or as a remote server and/or computing cloud (e.g., accessed over network 210). It is noted that correlation code 222A may be stored in data storage device 222, with executing portions loaded into memory 206 for execution by processor(s) 202.

Computing device 204 may include data interface 224, optionally a network interface, for connecting to network 210, for example, one or more of, a network interface card, a wireless interface to connect to a wireless network, a physical interface for connecting to a cable for network connectivity, a virtual interface implemented in software, network communication software providing higher layers of network connectivity, and/or other implementations. Computing device 204 may access one or more remote servers 218 using network 210, for example, to download updated correlation code 222A, and/or to download an updated version of image processing code 206A.

Computing device 204 may communicate using network 210 (or another communication channel, such as through a direct link (e.g., cable, wireless) and/or indirect link (e.g., via an intermediary computing device such as a server, and/or via a storage device) with one or more of:

Client terminal(s) 208, for example, when computing device 204 acts as a server providing correlation services (e.g., SaaS) to remote client terminals for analyzing images of target individual for computation of corresponding values that would otherwise be measured by a dynamometer without performing measurements by a dynamometer.

Server 218, for example, which may store a large number of images and associated dynamometer measured values for computing and/or updating the correlation code 222A.

Image and/or body part location repository 214, which may store a large number of images and/or body part locations and associated dynamometer measured values for computing and/or updating the correlation code 222A.

It is noted that imaging interface 220 and data interface 224 may exist as two independent interfaces (e.g., two network ports), as two virtual interfaces on a common physical interface (e.g., virtual networks on a common network port), and/or integrated into a single interface (e.g., network interface).

Computing device 204 and/or client terminal(2) 218 includes or is in communication with a user interface 226 that includes a mechanism designed for a user to enter data (e.g., select value to compute) and/or view the computed value. Exemplary user interfaces 226 include, for example, one or more of, a touchscreen, a display, a keyboard, a mouse, and voice activated software using speakers and microphone. The user interface 226 may be part of a mobile device in communication with computing device 204 (e.g., client terminal 208 and/or another mobile device), for example, a touchscreen of a smartphone and/or touchscreen of a tablet.

Referring now back to FIG. 1, at 102, correlation code 222A is provided and/or created. Correlation code 222A may be obtained, from example, from a server (e.g., 218) that creates and/or updates correlation code, from a storage device that is connected to computing device 204, and/or created by code executed by processor(s) 202 of computing device 204.

Correlation code 222A is stored on a non-transitory medium. Correlation code 222A includes code instructions for execution by hardware processors (e.g., processor(s) 202).

An exemplary method of creating the correlation code 222A is now described. Correlation code 222A is created based on empirical measurements performed by one or more dynamometer(s) on a population of sample individuals. The measurements performed by the dynamometer(s) are indicative of muscle strength of one or more muscles and/or muscle groups of each sample individual. The measurements are stored in a measurement dataset.

Image parameters are computed for each of the sample individuals based on captured images of the sample individual performing defined movements, as described with reference to acts 104-114 of FIG. 1. The image parameters are stored in an image-parameter dataset.

The values of the measurement dataset are correlated with the image parameter dataset to create the correlation code. The correlation may be performed, for example, by computation of a regression line (and/or other function) that correlates between the values of the measurement dataset and values of the image-parameter dataset, a map (e.g., vector, pointer, table of vales) that maps values of the image-parameter dataset to values of the measurement dataset, and by training a statistical classifier to output a measurement value for a certain input image-parameter according to training datasets that include the measurement dataset and image-parameter dataset. Exemplary statistical classifiers include: one or more neural networks of various architectures (e.g., artificial, deep, convolutional, fully connected, and combinations of the aforementioned), support vector machine (SVM), logistic regression, k-nearest neighbor, and decision trees.

Optionally, multiple types of correlation codes are created, for example, multiple regression lines (and/or other functions) and/or multiple classifiers. Each type may be based on measurements performed for a certain sub-group of the population, for example, according to one or more of: gender, age, fitness levels (e.g., athlete, fit, lack of regular exercise), and/or medical conditions (recovery from muscle injury, recovery from stroke) and/or evaluation type (e.g., to assess improvement in performance, functional and/or game technique).

At 104, images are captured of the target individual while the target individual is performing at least two defined movements. The images are captured by sensor(s) 212, for example, by a video camera, a still camera, and/or kinetic sensor. The images may be stored, for example, as video that includes 30 frames (or other number) per second. Each frame may be stored as digital images, for example, a .jpeg file (or other digital image storage format).

The defined movements may be defined according to states of a physical movement test. The defined movements may be performed repeatedly, for example, the individual may repeat the defined movement three times (or other number of times). The defined movements may be performed for one limb (i.e., left or right), for both limbs simultaneously, and/or alternatively for both limbs (i.e., first left and then right, or first right and then left).

The defined movements and/or physical movement test are determined according to the measured-parameter indicative of muscle strength ratio, and according to which movements are captured within images that are processed to compute the image-parameter which is correlated to the measure-parameter. For example, the user may select the desired measured-parameter from a GUI (e.g., by manually entering the measured-parameter, and/or selecting the measured-parameter from a list). In response, the GUI presents an indication of the defined movements to be performed in order to compute the measured-parameter from captured images of the target individual performing the defined movements.

The images in which the target individual is captured performing the defined moves are identified (and optionally extracted) from the multiple acquired images (e.g., from the video). Optionally, a single image is captured for each defined move. Alternatively or additionally, a set of images (e.g., two, three, or more images) are identified and optionally extracted) for each defined move.

The defined movement may be indicative of force proportion of target muscle(s), such as muscle groups, optionally complementary muscles. Exemplary defined target muscle groups include: flexors, extensors, abductors, adductors, internal rotators, external rotators. Exemplary defined movements indicative of force proportion include: flexion, extension, abduction, adduction, internal rotation, and external rotation. Flexion and/or extension may be measured as angles between two limbs attached to a joint, for example, relative to the elbow and/or knee joint. Abduction and/or adduction may be measured as angular rotation (e.g., in degrees) around a joint, for example, hip joint, knee joint, and/or wrist. Internal and/or external rotation may be measured as angular rotation (e.g., in degrees) of a body part, for example, shoulder, hip, trunk, neck, and/or arm. Exemplary body parts moved during the defined movements include: elbow joint and body parts connected to it, knee joint and body parts connected to it, hip joint and body parts connected to it, and combinations of the aforementioned.

For simplicity of explanation and without being necessarily limiting, two defined moves are described as being performed, identified in images, and processed to compute the image parameter. However, it is to be understood that three or more defined moves may be performed, identified in images, and processed to compute the image parameter.

Optionally, the first and second defined movements are of the same body part (e.g., joint, limb, other body portion) at different positions, optionally at varying degrees of resistance of the target muscle(s). Exemplary relationships between the first and second defined movements include:

The first defined movement is based on no significant resistance of the target muscle, and the second defined movement is based on at least some partial resistance of the target muscle(s).

The first defined movement is based on at least some partial resistance of the target muscle(s) and the second defined movement is based on no significant resistance of the target muscle(s).

The first defined movement is based on a partial resistance of the target muscle, and the second defined movement is based on a resistance of the target muscle greater than the partial resistance during the first defined movement. The resistance during the second defined movement may be a greater partial resistance, or a full resistance.

The second defined movement is based on a partial resistance of the target muscle, and the first defined movement is based on a resistance of the target muscle(s) greater than the partial resistance during the second defined movement. The resistance during the first defined movement may be a greater partial resistance, or a full resistance.

Exemplary defined movements are based on the single leg squat, where the first defined movement is an unsupported single leg squat (USLS), and the second defined movement is a supported single leg squat (SSLS). Other exemplary defined movements are based on one or more of the following: landing error scoring system (LESS), shoulder rotation, countermovement jump (CMJ), repetitive CMJ, full squat, single leg hop, single leg (SL)-drift, dorsiflexion, and Hip Rotation test. Further additional exemplary defined movements are based on performing natural activities include: running, climbing stairs, climbing a ladder, walking, and riding a bike.

At 106, body part locations of the target individual corresponding to the captured images are obtained.

The body part locations corresponding to the images may be identified, for example, by a 3D sensor that captures depth location data and optionally an associated visual image. Alternatively or additionally, the body part locations are computed from the images themselves, for example, by code that identifies the body parts within the images and comprise the location of each body part within a 2D and/or 3D coordinate system.

The body part locations may be indicative of the location of joint(s), limb(s), and/or other body parts (e.g., head, neck, spine, abdomen). The body part locations may be obtained from a skeletal analysis of the images. The body part locations may be represented within a two dimensional (2D) coordinate system, for example, represented by a 2D image in which the defined movements are captured, for example, frontal and/or sagittal plane. Alternatively or additionally, the body part locations may be represented within a three dimensional (3D) coordinate system, for example, representing the space within which the target individual is standing. The 3D locations may be computed based on multiple sensor(s) (e.g., cameras) that capture 2D images of the target individual from varying angles, and/or captured by a 3D sensor(s) (e.g., camera). The 3D locations may be computed based on output of a 3D kinetic sensor that captures depth data.

The body part locations may be computed according to an analysis of the images. For example, the body part locations may be outputted by a 3D kinematic sensor, and/or by code that analysis the images to identify physical visual markers positioned on the target individual, for computation of the 2D and/or 3D locations of the visual markers.

At 108, images depicting the defined movements are identified. Each of the identified images is associated with a respective set of body part locations. One set of body part locations corresponding to the image(s) depicting the first defined movement is identified and/or computed, and a second set of body part locations corresponding to the image(s) depicting the second defined movement is identified and/or computed.

The images depicting the defined movements may be identified from the video and/or multiple images. The locations of the body parts within the identified images are computed and/or extracted.

An exemplary automated method for obtaining the body part locations corresponding to the images depicting the defined movements is now described. The method may be implemented as code instructions executable by one or more hardware processors. One or more frame-values are computed for the captured images. The captured images may be frames extracted from the video. For example, frame-values are computed for all frames of the video capturing the target individual performing the defined movements according to the physical movement test. The frame-value(s) are computed for respective images (optionally each respective image) according to the body part locations corresponding to the respective image. The images depicting the target individual performing the defined movements are selected from the captures images (e.g., video) according to a set of rules applied to the frame-values. It is noted that alternatively, the user may manually select the images, for example, based on visual inspection. The selected images are termed stateframes, as each state-frame represents a certain state of the physical movement test corresponding to a certain defined movement. The images depicting the first and second defined movement are identified according to corresponding image state-frames based on a predefined order of the corresponding states of the physical movement test.

The frame-value(s) may be computed according to the body part locations associated with the images. Exemplary frame-values include: position of a certain joint, angle between different body parts, and/or angle at a joint.

State-frames are indicative of, for example, one or more of the following states that correspond to the defined movements of the examples of physical movement tests: Starting Position, and Maximum Displacement.

One or more state-frames are identified for each of the defined movements.

At 110, a respective image-metric is computed for each of the images (e.g., state-frames) identified as depicting each of the defined movements. At least two image-metrics are computed. For example, a first image-metric is computed for one image representing the first defined movement, and a second image-metric is computed for another image representing the second defined movement.

Each respective image-metric is computed according to the body part locations associated with the respective identified image (e.g., state-frame). The image-metric may be computed according to the frame-value(s), may be the same as the frame-value(s), or may be a value different than the frame-value(s).

Exemplary image-metrics include: joint angle, rotation amount, abduction amount, adduction amount, flexion amount, and extension amount.

At 112, one or more image-parameters are computed according to the image-metrics. Optionally, a single image-parameter is computed from multiple image-metrics indicative of the defined movements of the physical performance test.

At 114, the image-parameter is converted to an indirect estimate of a measured-parameter indicative of muscle strength of a target muscle(s) without directly being measured for the target individual by a dynamometer.

The conversion is performed according to the correlation code that correlates between image-parameters and measured-parameters. For example, the measured-parameter(s) is outputted by a statistical classifier that receives the image-parameter(s) as input, by mapping the image-parameter(s) to measured-parameter(s), and/or by a regression function (e.g., linear) that computes the measured-parameter for a give image-parameter.

The converting is performed without the target individual actually undergoing any measurements by the dynamometer.

Alternatively or additionally, the correlation code includes a statistical classifier that classifies the image-parameter into a classification category indicative of strength of a target muscle, rather that outputting a measured value. The classification category may be, for example, a verbal description (e.g., strong, normal, and weak), and/or a numerical category (e.g., on a scale of 1-10, where 10 denotes maximum strength and 1 denotes complete lack of strength). The classification category classifier may be trained by assigning a respective category to each empirically measured strength value.

Exemplary image-metrics computed from body locations of identified images (e.g., state-frames), a single image-parameter computed from multiple image-metrics, and a converted measured-parameter include:

The first image-metric is a value of an unsupported knee valgus (e.g., measured as degrees relative to the knee joint when the other leg is unsupported). The second image-metric is a value of a supported knee valgus (e.g., measured as degrees relative to the knee joint when the other leg is supported). The image-parameter is computed as: (supported knee valgus−unsupported knee valgus)/supported knee valgus×100. The image-parameter is correlated to the measured-parameter indicative of a hip adductor/abductor strength ratio.

The first image-metric is a value of an unsupported hip flexion (e.g., measured as degrees relative to the hip joint when one leg is unsupported). The second image-metric is a value of a supported hip flexion (e.g., measured as degrees relative to the hip joint when one leg is supported). The image-parameter is computed as: (supported hip flexion−unsupported hip flexion)/supported hip flexion×100. The image-parameter is correlated to the measured-parameter indicative of a hip extensor/flexor muscle strength ratio.

The first image-metric is a value of an unsupported anterior knee displacement. The second image-metric is a value of a supported anterior knee displacement. The image-parameter is computed as: (supported anterior knee displacement−unsupported anterior knee displacement)/supported anterior knee displacement×100. The image-parameter is correlated to the measured-parameter indicative of an eccentric hamstring/eccentric quadriceps muscle strength ratio.

The first image-metric is a value of a first maximal knee flexion (KF) during USLS. The second image-metric is a value of a second maximal KF during SSLS. The image-parameter is a dynamic knee ratio (DKR) denoting the percentage difference between the second maximal KF and the first maximal KF. The DKR is computed according to the relationship: DKR=(maximal KF during SLSS−maximal KF during USLS)/maximal KF during SLSS×100. The DKR is converted to a value of the measured-parameter indicative of hamstring muscle strength.

Optionally, the correlation code includes code for correlating between DKR and a concentric Hamstring/Quadriceps strength (H/Q) ratio. Alternatively or additionally, the correlation code includes code for a negative linear function for correlating between decreasing DKR values and increasing H/Q ratio values. Alternatively or additionally, the correlation code includes code for correlating between DKR and a concentric hamstring peak torque. Alternatively or additionally, the correlation code includes code for correlating between DKR and a concentric hamstring PT/BW (peak torque/body weight).

At 116, the computed measured-parameter is provided and/or outputted. The measure-parameter may be presented on a display of a client terminal, stored in a storage device (e.g., within an electronic medical record (EMR) of the target individual), and/or forwarded to remote server (e.g., for analysis by an expert). Optionally, an alert indicative of weakness in the target muscle group is generated. The alert may be generated when the value of the image-parameter is greater than (or less than) a threshold, and/or within a range.

The alert may be indicative of weakness in a first target muscle relative to a second target muscle when the image-parameter is greater than a threshold (or less than a threshold or within a range). For example, the alert is indicative of weakness in the hamstring muscle relative to the quadriceps muscle when the DKR is greater than a threshold.

The threshold for generating the alert may be selected according to a population that is matched to a profile of the target individual, for example, by one or more of: age, gender, fitness level, and medical condition. The population may be selected from the sample individuals that were evaluated for creation of the correlation code. The threshold may be selected, for example, according to the bottom twentieth (or other cutoff value) percentile values of the population, optionally, the matched population. Values above the threshold are indicative of increased risk of injury. An example of a threshold value for a general population is about 15-20%. An exemplary threshold for a young population is about 20-25%. AN exemplary threshold for a population of professional male athletes is about 10-15%.

The alert may be transmitted to a client terminal, for example, as a pop-up message appearing on the display, as an email, as an short message, and/or as an audio message (e.g., via an audio file and/or phone call). The alert may be stored in the EMR of the target individual, and/or transmitted to a server for further viewing by an expert (e.g., healthcare provider).

Optionally, multiple computed measured-parameters are computed over multiple spaced apart time intervals, for example, once a week, once a month, once every 3 months, once every 6 months, once a year, or other time intervals. A trend curve may be presented on a display (e.g., within a GUI) based on the multiple measured-parameters. Trends may be manually and/or automatically computed based on the trend curve, for example, a trend of the measured-parameter towards crossing the threshold, and/or whether measure-parameters that are above the threshold are trending downwards to below the threshold.

Various embodiments and aspects of the present invention as delineated hereinabove and as claimed in the claims section below find calculated support in the following examples.

EXAMPLES

Reference is now made to the following examples of computation of a dynamic knee ratio as an indicator of hamstring muscle strength during a single leg squat test based on captured images, without directly measuring application of force by a dynamometer, which together with the above descriptions illustrate some implementations of the systems, methods, apparatus, and/or code instructions described herein in a non-limiting fashion.

Inventors performed an experiment, based on some implementations of the systems, methods, apparatus, and/or code instructions described herein, to compare hamstring and quadriceps muscle strength to the percentage difference between maximal knee flexion (KF) in an unsupported single leg squat (USLS) and supported single leg squat (SSLS) to create a measure of dynamic knee stability (DKS). The experiment is designed to assess whether the difference between maximal knee flexion during an unsupported SLS and a supported SLS compares to thigh muscle strength and indicates a measure of dynamic knee stability. The greater the difference the less dynamic knee stability a person will have.

The ability of one to achieve increased knee flexion during an USLS takes an increased amount of dynamic knee stability. It is hypothesized that during a SSLS a person would have better dynamic knee stability and thus achieve a greater amount of KF. The hamstring muscles aid in dynamically stabilizing the knee joint, as well as their co-contraction with the quadriceps muscles, thus injury prevention requires sufficient hamstring strength and neuromuscular control. Therefore, by comparing thigh muscle strength to the percentage difference between maximal knee flexion in an unsupported and supported SLS a measure of dynamic knee stability is provided. The DKS enables the clinician to use the difference between the SSLS and USLS computed from captured digital images as an indirect alternative to isokinetic strength testing by a dynamometer to get an idea of dynamic knee control.

Twenty-six amateur athletes (24.6±8.4 years; 75.4±10.3 kg, 176.8±7.3 cm) who participated in running, football or sport on a regular basis and who did not present with any injuries to the lower extremity in the preceding year were included in the study. After signing an informed consent each person warmed-up on a cycling ergometer for 5 minutes. By combining the dominant and non-dominant sides, the total "legs" for analysis was n=52.

Using a 3D Kinect™ camera and validated, real-time, cloud-based Physimax™ technology based on captured images (i.e., extracted from a video) to capture the SLS, participants performed 3 repetitions of an unsupported SLS starting on their dominant leg and repeated on their non-dominant leg. Participants then performed 3 repetitions of a supported SLS, with their back leg supported on a 30 centimeter (cm) box behind them. Kinematics in the frontal and sagittal planes were reported as maximal knee flexion, maximal hip flexion, maximal knee valgus, maximal anterior knee displacement. The dynamic knee ratio was determined by calculating the percentage difference between supported and unsupported SLS: (supported KF−unsupported KF)/supported KF×100.

A Biodex™ System 4 dynamometer was used to assess concentric and eccentric quadriceps and hamstring strength at an angular velocity 60 deg/sec. Participants were seated with the seat back at 85 degrees and stabilized by straps to prevent unwanted movement. The anatomical position of the knee joint was set at 90 degrees and the dynamometer's fulcrum aligned with the lateral femoral condyle to allow for full range of motion (ROM). Participants warmed up prior to testing and performed trial repetitions prior to performing five maximal repetitions of concentric (CON) knee extension/flexion starting on the dominant side, followed by the non-dominant side. Following a 2-minute break, eccentric (ECC) knee extension/flexion was tested over 5 maximal repetitions. The following variables were recorded: CON and ECC hamstring and quadriceps peak torque, angle of peak torque, CON and ECC hamstring/quadriceps ratio, dynamic control ratio (ECC hamstrings/CON quadriceps) and PT/BW for CON and ECC hamstrings and quadriceps.

Descriptive statistics are represented as means and standard deviations. A linear regression was performed to determine if the dynamic knee ratio during a SLS could predict isokinetic hamstring strength. Pearson's correlations were used to determine an association between the degree of knee and hip flexion with hamstring and quadriceps muscle strength. A Mann-Whitney test was performed to determine if there was any difference between subjects who had a low or high concentric H/Q ratio and the dynamic knee ratio. Comparison between mean values was done using a Student's t-test. Level of significance was accepted at 95%.

Twenty-six healthy, amateur athletes participated in the study. The mean age was 24.6±8.4 years; mean weight was 75.4±10.3 kg; and mean height was 176.8±7.3 cm.

Maximal knee flexion was assessed during an unsupported and supported SLS (Table 1), with mean values being above the normal range of 55 degrees. Mean knee flexion during the supported SLS was significantly greater compared to the unsupported SLS (p=0.000059). Mean percentage difference of the maximal knee flexion angle between the supported and unsupported SLS was 13.3±14.5%.

Concentric and eccentric hamstring and quadriceps peak torque; peak torque to body weight; H/Q ratio and DCR are shown in Table 1. Mean H/Q ratios were within normal limits for both concentric and eccentric strength; however, the DCR was in a lower range.

Reference is now made to Table 1, which presents mean maximal knee flexion angles during the supported and unsupported SLS, and Concentric and Eccentric Quadriceps and Hamstring torque and strength ratios.

TABLE 1

| Variables | Unsupported SLS (n = 52) | Supported SLS (n = 52) |
|---|---|---|
| Maximal knee flexion angle (deg) | 78.1 ± 16.9* | 90.0 ± 11.6 |
| Dynamic knee ratio (%) | 13.3 ± 14.5 | |

| | Concentric (n = 52) | Eccentric (n = 52) |
|---|---|---|
| Quadriceps Peak Torque (Nm) | 199.4 ± 41.6 | 246.8 ± 57.9 |
| Hamstring Peak Torque (Nm) | 122.9 ± 27.5 | 147.6 ± 28.9 |
| Quadriceps Peak Torque/BW (Nm/kg) | 2.6 ± 0.5 | 3.3 ± 8.3 |
| Hamstring Peak Torque/BW (Nm/kg) | 1.6 ± 0.4 | 2.0 ± 4.2 |
| Hamstring/Quadriceps Ratio (%) | 61.3 ± 7.1 | 61.5 ± 11.8 |
| Dynamic Control Ratio | 0.7 ± 0.2 | |

*Significant difference knee flexion USLS vs SSLS: p = 0.000059

Figure 3:
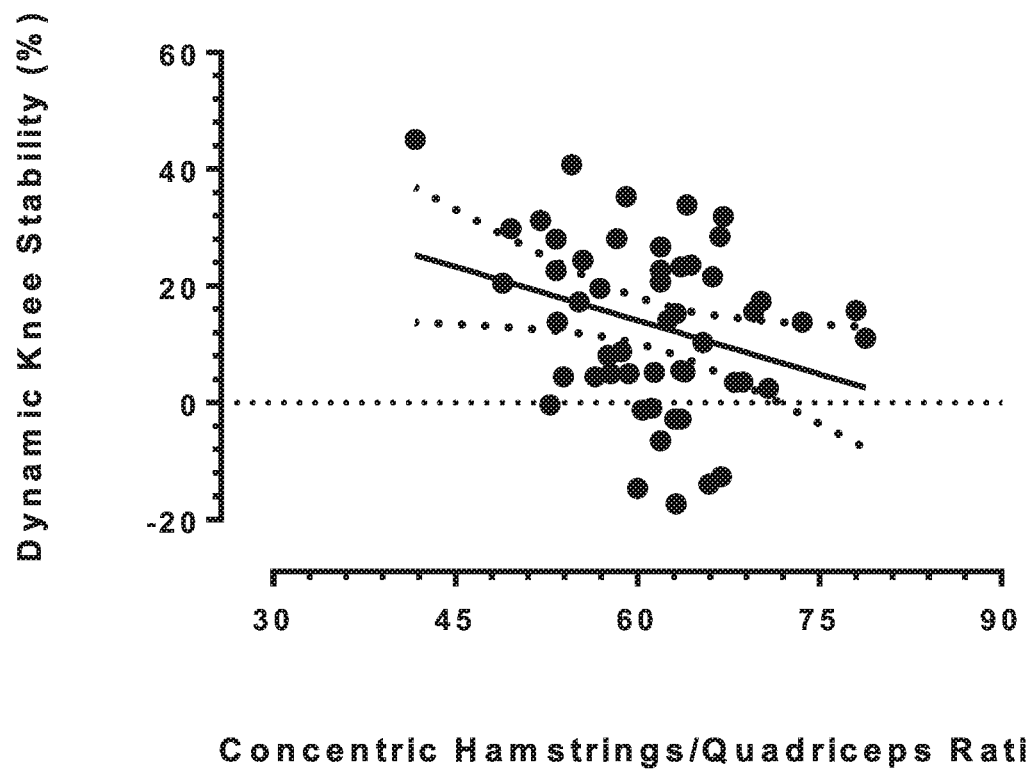
FIG. 3 is a graph of a linear regression between dynamic knee stability (%) computed from images and concentric hamstring to quadriceps muscle strength ratio (%) obtained by empirical isokinetic dynamometer measurements as part of an experiment, in accordance with some embodiments of the present invention.

Reference is now made to FIG. 3, which is a graph of a linear regression between dynamic knee stability (%) and concentric hamstring to quadriceps muscle strength ratio (%), where R=0.301 and p=0.030, in accordance with some embodiments of the present invention. The graph indicates a significant negative association between percentage difference in knee flexion during the USLS and SSLS and the concentric H/Q ratio.

The results presented in FIG. 3 indicate that as the % difference increases (thus a decrease in dynamic knee stability), there is a decrease in the H/Q ratio, thus the lower the hamstring strength the worse the dynamic knee stability. Therefore, in order to increase dynamic knee stability, one would need to strengthen the hamstring muscles. Furthermore, the imbalance of the hamstring muscles relative to the quadriceps muscles can indicate a lack of neuromuscular control around the knee joint.

Reference is now made to Table 2, which presents correlations between maximal knee flexion and hip flexion angle with strength measurements during an unsupported single leg squat (n=52).

TABLE 2

| | USLS Knee flexion (deg) | p-value |
|---|---|---|
| CON Hamstring PT (Nm) | R = 0.34 | 0.013 |
| CON Hamstring PT/BW (Nm/kg) | R = 0.30 | 0.034 |
| H/Q CON Ratio (%) | R = 0.41 | 0.003 |

| | USLS Hip Flexion (deg) | p-value |
|---|---|---|
| CON H/Q Ratio (%) | R = 0.35 | 0.0.11 |
| ECC H/Q Ratio (%) | R = 0.31 | 0.026 |
| ECC Quad PT (Nm) | R = −0.28 | 0.046 |

The results presented in Table 2 indicate significant positive correlations between degree of maximal knee flexion and concentric hamstring peak torque, concentric hamstring PT/BW and concentric H/Q ratio—indicating that the lower the degree of maximal knee flexion, the lower the concentric hamstring strength. Therefore, to increase maximal knee flexion one would need to strengthen the hamstrings concentrically. Significant positive correlations between degree in maximal hip flexion and concentric hamstring peak torque, concentric hamstring PT/BW and concentric H/Q ratio—indicates that to aid in increasing maximal hip flexion one needs to strengthen the hamstring muscles.

The experiment indicates that there is an association between the percentage difference in SSLS and USLS maximal knee flexion, which are computed from captured images of the target individual, and hamstring muscle strength which are otherwise measured via a dynamometer, without requiring the target user to undergo measurements by the dynamometer. As the dynamic knee ratio during a single leg squat becomes worse (percentage increases) the hamstring strength decreases. The hamstring muscles aid in dynamically stabilizing the knee joint and aid in preventing anterior translation of tibia on the femur. Furthermore, the relationship between the hamstring strength relative to the quadriceps muscle strength, provides an indication of how these muscles work in a coordinated way to stabilize the knee joint, and an imbalance between the muscles may indicate diminished neuromuscular control. Therefore, assessing the dynamic knee ratio during a single leg squat via images provides an indication of hamstring strength and thus control at the knee joint as would otherwise be measured via a dynamometer, without requiring the target user to undergo measurements by the dynamometer.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

It is expected that during the life of a patent maturing from this application many relevant dynamometers will be developed and the scope of the term dynamometer is intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A system for indirectly estimating a value indicative of muscle strength ratio between a first target muscle and a second target muscle of a target individual based on an analysis of a plurality of digital images, comprising:
a non-transitory memory having stored thereon a code for execution by at least one hardware processor of a computing device, the code comprising:
code for receiving, from at least one sensor, a video including a plurality of images and associated plurality of body part locations of a target individual corresponding to the plurality of images, wherein the video depicts the target individual performing a physical movement test comprising a first defined movement and a second defined movement;
code for identifying at least one first image of the plurality of imaged depicting the target individual performing the first defined movement, and obtaining a first set of body part locations associated with the at least one first image;
code for identifying at least one second image of the plurality of imaged depicting the target individual performing the second defined movement, and obtaining a second set of body part locations associated with the at least one second image;
code for computing a first image-metric according to the first set of body part locations associated with the at least one first image, and computing a second image-metric according to the second set of body part locations associated with the at least one second image;
code for computing a single image-parameter as a function of the first image-metric and the second image-metric; and
code for converting the single image-parameter to an estimate of a measured-parameter indicative of a muscle strength measurement ratio between a first target muscle obtained by a dynamometer to a second target muscle obtained by the dynamometer, according to correlation code that correlates between values of the single image-parameter and measured-parameters obtained based on the dynamometer performing empirical measurements of application of an exerted force of the first and second target muscles by each of a plurality of other subjects.

2. The system according to claim 1, wherein the first defined movement is based on no significant resistance of a target muscle, and wherein the second defined movement is based on at least partial resistance of the target muscle.

3. The system according to claim 1, wherein the first defined movement is based on a first partial resistance of a target muscle, and wherein the second defined movement is based on a second resistance of the target muscle greater than the first partial resistance.

4. The system according to claim 1, wherein the first defined movement and the second defined movement are indicative of force proportion of muscle groups.

5. The system according to claim 4, wherein the first defined movement and the second defined movement indicative of force proportion of muscle groups are selected from the group consisting of: flexion, extension, abduction, adduction, internal rotation, external rotation.

6. The system according to claim 1, wherein the first image-metric and the second-image metric are selected from the group comprising: joint angle, rotation amount, abduction amount, adduction amount, flexion amount, and extension amount.

7. The system according to claim 1, wherein the first defined movement comprises an unsupported single leg squat (USLS) and the second defined movement comprises a supported single leg squat (SSLS).

8. The system according to claim 7, wherein the first image-metric comprises an unsupported knee valgus, the second image-metric comprises a supported knee valgus, and the image-parameter is computed as: (supported knee valgus−unsupported knee valgus)/supported knee valgus× 100, wherein the image-parameter is correlated to the measured-parameter indicative of a hip adductor/abductor strength ratio.

9. The system according to claim 7, wherein the first image-metric comprises an unsupported hip flexion, the second image-metric comprises a supported hip flexion, and the image-parameter is computed as: (supported hip flexion−unsupported hip flexion)/supported hip flexion×100, wherein the image-parameter is correlated to the measured-parameter indicative of a hip extensor/flexor muscle strength ratio.

10. The system according to claim 7, wherein the first image-metric comprises an unsupported anterior knee displacement, the second image-metric comprises a supported anterior knee displacement, and the image-parameter is computed as: (supported anterior knee displacement−unsupported anterior knee displacement)/supported anterior knee displacement×100, wherein the image-parameter is correlated to the measured-parameter indicative of an eccentric hamstring/eccentric quadriceps muscle strength ratio.

11. The system according to claim 7, wherein the first image-metric comprises a first maximal knee flexion (KF) during USLS, and the second image-metric comprises a second maximal KF during SSLS, wherein the image-parameter comprises a dynamic knee ratio (DKR) denoting the percentage difference between the second maximal KF and the first maximal KF, and wherein the DKR is converted to a value indicative of hamstring muscle strength.

12. The system according to claim 11, wherein the correlation code includes code for correlating between DKR and a concentric Hamstring/Quadriceps strength (H/Q) ratio.

13. The system according to claim 11, wherein the correlation code includes code for a negative linear function for correlating between decreasing DKR values and increasing H/Q ratio values.

14. The system according to claim 11, wherein the correlation code includes code for correlating between DKR and a concentric hamstring peak torque.

15. The system according to claim 11, wherein the correlation code includes code for correlating between DKR and a concentric hamstring PT/BW (peak torque/body weight).

16. The system according to claim 11, further comprising code for generating an alert indicative of weakness in the hamstring muscle relative to the quadriceps muscle when the DKR is greater than a threshold.

17. The system according to claim 11, further comprising code for computing the DKR according to the relationship: DKR=(maximal KF during SLSS−maximal KF during USLS)/maximal KF during SLSS×100.

18. The system according to claim 1, further comprising code for generating an alert indicative of weakness in a first target muscle relative to a second target muscle when the image-parameter is greater than a threshold selected according to a population that is matched to a profile of the target individual.

19. The system according to claim 18, wherein the threshold is about 15-20%.

20. The system according to claim 18, wherein the threshold is selected according to the bottom twentieth percentile values of the population.

21. The system according to claim 1, wherein the converting is performed without the target individual undergoing measurements by the dynamometer.

22. The system according to claim 1, wherein the dynamometer comprises an isokinetic strength testing device.

23. The system according to claim 1, further comprising code for computing the first and second set of body part locations from at least one of frontal and sagittal plane two dimensional (2D) images.

24. The system according to claim 1, wherein the first and second set of body part locations include 3D body joint locations.

25. The system according to claim 1, wherein the correlation code includes a statistical classifier that classifies the image-parameter into a classification category indicative of strength of a target muscle.

26. The system according to claim 1,
wherein the selecting of the at least one first image and the at least one second image from the video comprises:
computing at least one frame-value for each of the plurality of images, each frame-value computed according to the body part locations of the target individual;
analyzing the at least one frame value computed for each of the plurality of images to identify a plurality of image state-frames, each image state-frame corresponding to a certain state of a plurality of states of the certain physical movement test; and
identifying the first and second defined movements according to corresponding image state-frames based on a predefined order of the corresponding plurality of states of the physical movement test.

27. The system according to claim 26, wherein the analyzing is performed according to a set-of-rules applied to the at least one frame-value.

28. The system according to claim 27, wherein the certain state of the plurality of states is selected from the group consisting of Starting Position, and Maximum Displacement.

29. The system according to claim 27, wherein the at least one frame value is selected from the group consisting of:

position of at least one joint, angle of at least one joint, and angle between at least two body parts.

30. The system according to claim 1, wherein the first defined movement and the second defined movement are based on one or more members of the group consisting of: LESS, Shoulder Rotation, CMJ, Repetitive-CMJ, Single Leg Squat test, Full squat, single leg hop, SL-drift, and Dorsiflexion test, Hip Rotation test.

31. The system according to claim 1, wherein the at least one sensor comprises at least one video camera that captures the video and code for analyzing the video for computing the body location data.

32. The system according to claim 1, wherein the at least one sensor comprises a 3D kinetic sensor that captures the video and captures depth data, wherein the depth data is mapped to the video, wherein the body part locations are computed according to the depth data.

33. The system according to claim 1, wherein the plurality of images are selected from the group consisting of: visual images captured by at least one visual sensor, depth images captured by at least one depth sensor, and infrared images captured by at least one infrared sensors.

34. A method of indirectly estimating a value indicative of muscle strength ratio between a first target muscle and a second target muscle of a target individual based on an analysis of a plurality of digital images, comprising:
receiving, from at least one sensor, a video including a plurality of images and associated plurality of body part locations of a target individual corresponding to the plurality of images, wherein the video depicts the target individual performing a physical movement test comprising a first defined movement and a second defined movement;
identifying at least one first image of the plurality of imaged depicting the target individual performing the first defined movement, and obtaining a first set of body part locations associated with the at least one first image;
identifying at least one second image of the plurality of imaged depicting the target individual performing the second defined movement, and obtaining a second set of body part locations associated with the at least one second image;
computing a first image-metric according to the first set of body part locations associated with the at least one first image, and computing a second image-metric according to the second set of body part locations associated with the at least one second image;
computing a single image-parameter as a function of the first image-metric and the second image-metric; and
converting the single image-parameter to an estimate of a measured-parameter indicative of a muscle strength measurement ratio between a first target muscle obtained by a dynamometer and a second target muscle obtained by the dynamometer, according to correlation between values of the single image-parameter and measured-parameters obtained based on the dynamometer performing empirical measurements of application of an exerted force of the first and second target muscles by each of a plurality of other subjects.

35. A system for indirectly estimating a value indicative of muscle strength ratio of at least one target muscle of a target individual based on an analysis of a plurality of digital images, comprising: a non-transitory memory having stored thereon a code for execution by at least one hardware processor of a computing device, the code comprising: code for receiving, from at least one sensor, a video including a plurality of images and associated plurality of body part locations of a target individual corresponding to the plurality of images, wherein the video depicts the target individual performing a physical movement test comprising a first defined movement and a second defined movement; code for identifying at least one first image of the plurality of imaged depicting the target individual performing the first defined movement, and obtaining a first set of body part locations associated with the at least one first image; code for identifying at least one second image of the plurality of imaged depicting the target individual performing the second defined movement, and obtaining a second set of body part locations associated with the at least one second image, wherein the first defined movement comprises an unsupported single leg squat (USLS) and the second defined movement comprises a supported single leg squat (SSLS); code for computing a first image-metric according to the first set of body part locations associated with the at least one first image, and computing a second image-metric according to the second set of body part locations associated with the at least one second image, wherein the first image-metric comprises a first maximal knee flexion (KF) during USLS, and the second image-metric comprises a second maximal KF during SSLS, wherein the image-parameter comprises a dynamic knee ratio (DKR) denoting the percentage difference between the second maximal KF and the first maximal KF, and wherein the DKR is converted to a value indicative of hamstring muscle strength; code for computing an image-parameter according to the first image-metric and the second image-metric; and code for converting the image-parameter to an estimate of a measured-parameter indicative of strength measurement ratios of the at least one target muscle obtained by a dynamometer, according to correlation code that correlates between image-parameters and measured-parameters obtained based on the dynamometer performing empirical measurements of application of an exerted force of the at least one target muscle by each of a plurality of other subjects; and at least one of: (i) wherein the correlation code includes code for correlating between DKR and a concentric Hamstring/Quadriceps strength (H/Q) ratio, and (ii) code for computing the DKR according to the relationship: DKR= (maximal KF during SLSS−maximal KF during USLS)/ maximal KF during SLSS×100.

* * * * *